ns Cited | 260/546 | ofis|

United States Patent [19]

Suzukamo et al.

[11] Patent Number: 4,812,264
[45] Date of Patent: Mar. 14, 1989

[54] METHOD FOR RACEMIZATION OF OPTICALLY ACTIVE CHRYSANTHEMIC ACID DERIVATIVES

[75] Inventors: Gohfu Suzukamo, Osaka; Masami Fukao, Shiga; Yoji Sakito, Hyogo, all of Japan

[73] Assignee: Sumitomo Chemical Company, Limited, Osaka, Japan

[21] Appl. No.: 187,249

[22] Filed: Apr. 28, 1988

[30] Foreign Application Priority Data

Apr. 28, 1987 [JP] Japan ................. 62-105752
Apr. 28, 1987 [JP] Japan ................. 62-105753
Apr. 30, 1987 [JP] Japan ................. 62-109515
Apr. 30, 1987 [JP] Japan ................. 62-109516
Jun. 10, 1987 [JP] Japan ................. 62-145467

[51] Int. Cl.$^4$ ............................................. C07C 5/00
[52] U.S. Cl. ............................. 260/544 L; 260/546
[58] Field of Search ...................... 260/544 L, 546

[56] References Cited

U.S. PATENT DOCUMENTS 3,285,950 11/1966 Weber ................. 260/544 L
3,786,052 1/1974 Martel ................. 260/544 L
3,989,750 11/1976 Nagase ................ 260/544 L 4,485,257 11/1984 Suzuhomo .

Primary Examiner—Paul J. Killos
Attorney, Agent, or Firm—Birch, Stewart, Kolasch & Birch

[57] ABSTRACT

Racemization of an optically active chrysanthemic acid derivatives of the formula:

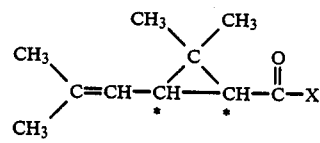

wherein X represents a chlorine atom, bromine atom or 2,2-dimethyl-3-isobutenyl-cyclopropane carboxyl group and * mark represents asymmetric carbon atom, is effected by contacting the acid derivatives with at least one compound selected from the group consisting of hydrogen bromide, a carboxylic acid bromide, an N-bromine compound, an S-bromine compound, a halobromine compound, a silicon-bromide compound, a phosphorus-bromide compound and an SH compound in the presence of a peroxide or an azo compound.

24 Claims, No Drawings

METHOD FOR RACEMIZATION OF OPTICALLY ACTIVE CHRYSANTHEMIC ACID DERIVATIVES

The present invention relates to a method for preparing racemized chrysanthemic acid derivatives useful as an intermediate for pyrethroid insecticides useful as low toxic, quickly effective insecticides. More particularly, it relates to a method for preparing racemized chrysanthemic acid derivatives by treating an optically active chrysanthemic acid derivatives of the formula:

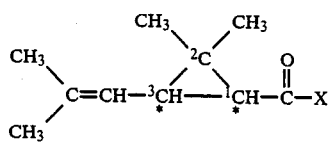

(wherein X represents a chlorine atom, a bromine atom or 2,2-dimethyl-3-isobutenyl-cyclopropane carboxyl group and * mark shows asymmetric carbon atom), which comprises contacting with at least one compound selected from hydrogen bromide, carboxylic acid bromides, silicon bromide compounds, S-bromine compounds, N-bromine compounds, halo-bromine compounds, phosphorus-bromide compounds and SH compounds in the presence of a peroxide or an azo compound.

Chrysanthemic acid constitutes an acid component of esters well-known as so-called pyrethroid insecticides, such as pyrethrin, allethrin, phthalthrin, etc., which are utilized as low mammalian toxic, quckly effective insecticides, and the chrysanthemic acid derivatives represented by the above formula (I) is useful as intermediate of these pyrethroid insecticides.

The chrysanthemic acid has four isomers, that is, two geometrical isomers, i.e. cis and trans forms, each of which respectively has two optical isomers, i.e. (+) and (−) forms. It has been known that, in general, among the isomers the pyrethroid esters composed of trans-form acid exhibit stronger insecticidal activity than those composed of the corresponding cis-form acid, furthermore, the esters composed of (+)−form acid exhibit exceedingly higher activity than those composed of the corresponding (−)-isomer.

In general, chrysanthemic acid is industrially produced as a mixture of cis and trans forms, each of which is in the form of racemic modification, namely, as (±)-form. Optical resolution of the thus-synthesized acid by means of an optically active organic base is conducted to obtain the (+)-form acid which is converted to an acid halide which is utilized for the preparation of insecticidal compounds with a higher activity. The remaining (−)-isomer is little useful, since the esters composed thereof is almost inactive. Accordingly, it is a problem to be solved in the production of the (±)-form acid, particularly in a commercial scale, that the (−)-form acid should be converted to more active (±)-form acid for effective utilization thereof.

For conversion to (±)-form, namely, racemic form, the inventors proposed a method in which optically active chrysanthemic acid is converted to the corresponding acid halide and then contacted with a Lewis acid such as aluminum chloride, aluminum bromide or zinc chloride as a catalyst (U.S. Pat. Nos. 3,989,750 and 4,182,906).

After an extensive study, the inventors have found that racemization of optically active chrysanthemic acid halide or its acid anhydride proceds by bringing them into contact with at least one compound selected from hydrogen bromide, carboxylic acid bromides, silicon bromides, S-bromine compounds, N-bromine compounds, halo-bromine compounds, phosphorus bromide compounds and SH compounds in the presence of a peroxide or an azo compound. The present invention has been established on the basis of such finding and additional researches.

That is, the present invention provides a method for preparing racemized chrysanthemic acid derivatives by treating an optically active chrysanthemic acid derivatives having the formula (I):

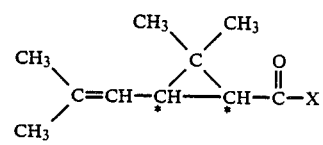

wherein X represents a chlorine atom, a bromine atom or 2,2-dimethyl-3-isobutenyl-cyclopropane carboxyl group and * mark represents asymmetric carbon atom, which comprises contacting with at least one compound selected from the group consisting of hydrogen bromide, a carboxylic acid bromide, an N-bromine compound, an S-bromine compound, a halo-bromine compound, a siliconbromide compound, a phosphorus-bromide compound and an SH compound in the presence of a peroxide or an azo compound.

The method of the present invention will more fully be described hereafter.

The optically active chrysanthemic acid derivatives represented by the formula (I) which are starting materials in the present invention include chrysanthemic acid chloride and chrysanthemic acid bromide and chrysanthemic acid anhydride.

In the present invention, any of the four isomers of chrysanthemic acid derivatives can be used solely or in mixtures of isomers at optional ratios and those of any degree in optical purity may be used. Needless to say, however, it is preferred to use carboxylic aid halides or acid anhydrides of (−)-form or rich in (−)-form.

Hydrogen bromide used as a catalyst in the present invention may be in the form of a gas or a solution in a solvent or may be produced in reaction system from a bromide such as lithium bromide or sodium bromide and an acid such as sulfuric acid.

Carboxylic acid bromides, a catalyst in the present invention, are usually those having 1–18 carbon atoms. They include, for example, aliphatic carbonyl bromides such as acetyl bromide, propionyl bromide, butyryl bromide, isobutyryl bromide, valeryl bromide, isovaleryl bromide, pivaloyl bromide, hexanoyl bromide, heptanoyl bromide, cyclohexanecarbonyl bromide, octanoyl bromide, nonanoyl bromide, decanoyl bromide, 3-(2-methylpropenyl)-2,2-dimethylcyclopropanecarbonyl bromide, undecanoyl bromide, palmitoyl bromide and stearoyl bromide; aliphatic dicarboxylic acid dibromides such as malonyl dibromide, succinyl dibromide, glutaryl dibromide, adipoyl dibromide, pimeloyl dibromide, suberoyl dibromide, azelaoyl dibromide and sebacoyl dibromide; acid bromides of mono and dicarboxylic acids having aromatic group such as benzoyl bromide, phenylacetyl bromide, phenylpropionyl bromide, phenylbutyryl bromide, naphthalenecarbonyl bromide, phthaloyl dibromide, terephthaloyl dibromide and isophthaloyl dibromide.

Examples of the silicon bromides used as a catalyst are lower alkylsilyl bromides such as trimethylsilyl bromide, dimethylsilyl dibromide, methylsilyl tribromide, triethylsilyl bromide, diethylsilyl dibromide and dimethyl-t-butylsilyl bromide; arylsilyl bromide such as triphenyl silyl bromide, and silyl tetrabromide.

N-bromine compounds as a catalyst are, for example, N-bromosuccinimide, N-bromoacetamide, N-bromopropionamide, N-bromobutyramide and N-bromovaleramide.

S-bromine compounds as a catalyst are, for example, thionyl bromide, sulfuryl bromide, p-toluenesulfonyl bromide, arylsulfinyl bromides such as phenylsulfinyl bromide and lower alkylsulfonyl bromides such as methanesulfonyl bromide.

Halo-bromine compounds as a catalyst are, for exampe, bromine, iodine monobromide and iodine tribromide.

P-bromide compounds are, for example, phosphorus tribromide, phosphorus pentabromide, phosphorus oxybromide, bromodiphenyl phosphine, dibromophenyl phosphine and dibromomethoxy phosphine.

Among these bromine compounds, preferred are hydrogen bromide, carboxylic acid bromides, S-bromine compounds, Si-bromide compounds and P-bromide compounds.

SH compounds as a catalyst in the present invention may be any of those containing —SH group. Thiols, carbothioic acids and carbodithioic acid are usually used. They are, for example, aromatic thiols such as thiophenol, o-, m- and p-thiocresols, o-, m- and p-methoxybenzene thiols, 1- and 2-naphthalenethiols, dithiocatechol, dithiorescorcin and dithiohydroquinone; aralkylthiols such as benzyl mercaptane; alkyl thiols such as methanethiol, ethanethiol, 1-propanethiol, 2-propanethiol, butanethiol, pentanethiol, hexanethiol, heptanethiol, octanethiol, nonanethiol, decanethiol, dodecanethiol, dithiothritol, ditioerythritol and butanedithiol; thiolcarboxylic acids such as thioglycolic acid, thiosalicylic acid, thiolactic acid and thiomalic acid; thiocarboxylic acids such as thioacetic acid, thiopropionic acid, thiobutyric acid and thiobenzoic acid and dithio acids such as dithioacetic acid, dithiopropionic acid, dithiobutyric acid and dithiobenzoic acid.

Preferred are aromatic thiols, thiolcarboxylic acids, thiocarboxylic acids and dithio acids. More preferred are thiophenol, thiocresol, thiosalicylic acid and thiobenzoic acid.

Compounds to be used as a catalyst are used in an amount within the range of 1/1000 ¼ mol, preferably 1/200 1/6 mol per 1 mol of chrysanthemic acid halide. When a compound to be racemized is chrysanthemic acid anhydride, an amount of the compounds for catalyst is preferably about two times as much as that required for chrysanthemic acid halide.

These catalysts are employed together with co-catalysts such as peroxides and azo compounds.

Peroxides are, for example, hydrogen peroxide, hydroperoxides such as t-butyl hydroperoxide, 1,1,3,3-tetramethylbutyl hydroperoxide, cumene hydroperoxide and diisopropylbenzene hydroperoxide, hydroperoxides produced by oxidation of ethers such as tetrahydrofuran and dioxane, diacyl peroxides such as benzoyl peroxide and lauroyl peroxide, peroxy esters such as t-butyl perbenzoate, t-butyl peracetate, diisopropyl peroxydicarbonate and dicyclohexyl peroxydicarbonate, ketone peroxides such as methyl ethyl ketone peroxide and cyclohexanone peroxide, dialkyl peroxides such as di-t-butyl peroxide and dicumyl peroxide, peracids such as peracetic acid. Of these peroxides, preferred are diacyl peroxides, peroxy esters, hydrogen peroxide and hydroperoxides.

Azo compounds include azonitriles such as azobisisobutylonitrile, 2,2'-azobis(2,4-dimethylvaleronitrile), 1,1'-azobis(cyclohexane-1-carbonitrile), 4,4'-azobis-4-cyanopentanoic acid, 2-phenylazo-2,4-dimethyl-4-methoxyvaleronitrile and 2-cyano-2-propylazoformamide; azo-esters such as methyl azobisisobutyrate and alkylazo compounds such as azo-t-butane. Azo-nitriles and azo-esters are preferable.

These peroxides and azo compounds are usually used, in an amount from 1/20 to 5 mol, preferably 1/10 to 2 mol, per mol of said catalyst.

The present racemization reaction is preferably carried out in the presence of an inert solvent. The solvents include saturated aliphatic hydrocarbons, aromatic hydrocarbons and their halide compounds, ethers, etc. These solvents can also be those used in esterification step and so when these are used in racemization step, reaction mass as such can be reacted with pyrethroid alcohol.

Reaction temperature varies depending on the catalyst and co-catalyst employed. The temperature ranges usually from −30° C. to boiling point of the chrysanthemic acid derivatives or boiling point of the solvent when it is employed. Preferable temperatures are −20° C. to 100° C. and 50° to 140° C. when the chrysanthemic acid derivatives are chrysanthemic acid halides and chrysanthemic acid anhydride, respectively.

The reaction time varies depending on amounts and varieties of the catalyst and co-catalyst employed and reaction temperature, too, but usually ranges from a few minutes to 10 hours.

In carrying out the method of the present invention, for example, the chrysanthemic acid derivatives and peroxide or azo compound are dissolved in a solvent and then thereto added catalyst or the derivatives are dissolved in a solvent and then thereinto are added in parallel the catalyst together with peroxide or azo compound. When chrysanthemic acid bromide is used as a substrate, usually this is dissolved in a solvent and then thereto is added a peroxide or azo compound.

Progress of the reaction can be determined by sampling a portion of reaction mixture and measuring optical rotation thereof or analysis by gas chromatography.

Thus, racemized chrysanthemic acid derivatives are prepared. According to the present invention, (−)-isomer of chrysanthemic acid derivatives represented by the formula (I) which is almost inactive when converted to pyrethroid or chrysanthemic acid derivatives rich in the (−)-isomer can be converted into racemic form with high efficiency and besides, the thus obtained acid derivatives have high purity. Therefore, various pyrethroids can be produced more simply and in high yields by reacting the resulting acid halide as such with various pyrethroid alcohols.

Furthermore, the resulting racemic mixture is converted into chrysanthemic acid by hydrolysis, which can be further converted into useful (+)-form by various optical resolutions.

In addition, the racemic mixture obtained by the method of the present invention is rich in trans isomer which is more effective and thus, the method of the present invention is also advantageous in this respect.

The present method can also be used for conversion of racemic cis-isomer or racemic mixture of cis- and trans-isomers of chrysanthemic acid derivatives into the corresponding racemic trans-rich isomer.

The following examples will further explain the present invention.

EXAMPLE 1

In a 100 ml flask were charged 5.0 g of (−)-rich chrysanthemic acid chloride (composition: (+)−cis, 0.7%; (−)-cis, 17.5%; (+)-trans, 3.7%; and (−)trans 78.1%), 40.0 g of toluene and 43.5 mg of t-butyl hydroperoxide under nitrogen and thereto was added dropwise 1 ml of a solution of hydrogen bromide (110 mg) in dioxane at 20°–25° C.

After stirring at the same temperature for 30 minutes, a portion of the reaction mixture was sampled and converted into d-2-octyl ester by a conventional method. Gas chromatography assay of the chrysanthemic acid gave the following optical isomer ratio: (+)-cis, 3.9%; (−)-cis, 3.9%; (+)-trans, 45.9%; and (−)-trans, 46.3%. Amount of chrysanthemic acid chloride in the reaction mixture was 4.88 g.

EXAMPLE 2

In a 100 ml flask were charged 5.0 g of (−)-cis chrysanthemic acid chloride and 40 g of toluene under nitrogen and then thereto were added in parallel 1 ml of a solution of t-butyl hydroperoxide (43.5 mg) in toluene and 1 ml of a solution of hydrogen bromide (87 mg) in dioxane over a period of 10 minutes at 20°–25° C. with stirring, followed by stirring at the same temperature for 20 minutes. A portion of the reaction mixture was sampled and converted into d-2-octyl ester by a conventional method. Gas chromatography assay gave the following optical isomer ratio: (+)-cis, 3.8%; (−)-cis, 4.2%; (+)-trans, 46.0%; and (−)-trans, 46.0%. The reaction mixture contained 4.93 g of chrysanthemic acid chloride

EXAMPLE 3

In a 100 ml flask were charged 2.5 g of (−)rich chrysanthemic acid bromide (composition: (+)-cis, 3 3%; (−)-cis, 5.1%; (+)-trans, 32.4%; and (−)-trans, 59.3%) and 25.6 g of dioxane under nitrogen and thereto was added dropwise 1 ml of a solution of t-butyl hydroperoxide (20 mg) in dioxane with stirring at 20°–25° C.

After stirring at the same temperature for 30 minutes, a portion of the reaction mixture was sampled and converted into d-2-octyl ester. Gas chromatography assay of the chrysanthemic acid gave the following optical isomer ratio: (+)-cis, 6.0%; (−)-cis, 6.3%; (+)-trans, 42.9%; and (−)-trans 44.8%.

EXAMPLE 4

In a 100 ml flask were charged 2.5 g of (−)-rich chrysanthemic acid chloride (composition: (+)-cis, 2.2%; (−)-cis, 14.8%; (+)-trans, 11.9%; and (−)-trans 71.1%), 24.1 g of dioxane and 0.12 g of t-butyl hydroperoxide and thereto was added dropwise 0.25 g of acetyl bromide with stirring at 20°–25° C.

After stirring at the same temperature for 30 minutes, a portion of the reaction mixture was sampled and converted into d-2-octyl ester by a conventional method. Gas chromatography assay of the chrysanthemic acid gave the following optical isomer ratio: (+)-cis, 3.8%; (−)-cis, 4.1%; (+)-trans, 44.6%; and (−)-trans, 47.5%.

EXAMPLE 5

In a 100 ml flask were charged 2.5 g of the same (−)-rich chrysanthemic acid chloride as used in Example 1, 25.6 g of dioxane and 121 mg of t-butyl hydroperoxide under nitrogen and thereto was added dropwise 0.42 g of thionyl bromide with stirring at 20°–25° C.

After stirring at the same temperature for 30 minutes, a portion of the reaction mixture was sampled and converted into d-2-octyl ester by a conventional method. Gas chromatography assay of the chrysanthemic acid gave the following optical isomer ratio: (+)-cis, 4.0%; (−)-cis, 4.3%; (+)-trans, 44.3%; and (−)-trans, 47.4%.

EXAMPLE 6

In a 100 ml flask were charged 2.5 g of the same (−)-rich chrysanthemic acid chloride as used in Example 1, 25.6 g of dioxane and 60 mg of t-butyl hydroperoxide under nitrogen and thereto was added dropwise 0.31 g of the same chrysanthemic acid bromide as used in Example 3 with stirring at 20°–25° C.

After stirring at the same temperature for 30 minutes, a portion of the reaction mixture was sampled and converted into d-2-octyl ester by a conventional method. Gas chromatography assay of the chrysanthemic acid gave the following optical isomer ratio: (+)-cis, 4.1%; (−)-cis, 4.4%; (+)-trans, 44.5%; and (−)-trans, 47.0%.

EXAMPLE 7

In a 50 ml flask were charged 2.5 g of the same (−)-rich chrysanthemic acid chloride as used in Example 1, 10.4 g of toluene and 60 mg of t-butyl hydroperoxide under nitrogen and thereto was added dropwise 0.21 g of bromine with stirring at 20°–25° C.

After stirring at the same temperature for 30 minutes, a portion of the reaction mixture was sampled and converted into d-2-octyl ester by a conventional method. Gas chromatography assay of the chrysanthemic acid gave the following optical isomer ratio: (+)-cis, 3.9%; (−)-cis, 4.4%; (+)trans, 45.5%; and (−)-trans, 46.2%.

EXAMPLE 8

In a 100 ml flask were charged 2.5 g of the same (−)-rich chrysanthemic acid chloride as used in Example 1, 30 g of dioxane and 8.4 mg of 60% aqueous hydrogen peroxide under nitrogen and thereto was added dropwise 3 ml of a solution of hydrogen bromide (0.32 g) in dioxane at 20°–25° C.

After stirring at the same temperature for 30 minutes, a portion of the reaction mixture was smapled and converted into d-2-octyl ester by a conventional method. Gas chromatography assay of the chrysanthemic acid gave the following optical isomer ratio: (+)-cis, 4.3%; (−)-cis, 4.4%; (+)-trans, 45.2%; and (−)-trans, 46.1%.

EXAMPLE 9

In a 100 ml flask were charged 2.5 g of the same (−)-rich chrysanthemic acid chloride as used in Example 1, 21.8 g of toluene and 0.14 g of t-butyl perbenzoate under nitrogen and thereto was added dropwise 1.6 ml of a solution of hydrogen bromide (0.16 g) in dioxane at 70°–75° C.

After stirring at the same temperaure for 30 minutes, a portion of the reaction mixture was sampled and converted into d-2-octyl ester by a conventional method. Gas chromatography assay of the chrysanthemic acid gave the following optical isomer ratio: (+)-cis, 4.7%; (−)-cis, 6.6%; (+)-trans, 37.2%; and (−)-trans, 51.5%.

EXAMPLE 10

In a 100 ml flask were charged 2.5 g of the same (−)-rich chrysanthemic acid chloride as used in Example 1, 21.8 g of benzene and 0.11 g of azobisisobutyronitrile under nitrogen and thereto was added dropwise 1.7 ml of a solution of hydrogen bromide (0.17 g) in dioxane at 70°–75° C.

After stirring at the same temperature for 30 minutes, a portion of the reaction mixture was sampled and converted into d-2-octyl ester by a conventional method. Gas chromatography assay of the chrysanthemic acid gave the following optical isomer ratio: (+)-cis, 4.7%; (−)-cis, 4.9%; (+)-trans, 44.5%; and (−)-trans, 45.9%.

EXAMPLE 11

In a 50 ml flask were charged 1.0 g of the same (−)-rich chrysanthemic acid chloride as used in Example 4, 5 ml of toluene and 0.088 g of azobisisobutyronitrile under nitrogen and thereto was added dropwise 1 ml of a solution of N-bromosuccinimide (0.095 g) in acetone with stirring at 78° C.

After stirring at the same temperature for 30 minutes, a portion of the reaction mixture was sampled and converted into d-2-octyl ester by a conventional method. Gas chromatography assay of the chrysanthemic acid gave the following optical isomer ratio: (+)-cis, 5.7%; (−)-cis, 6.1%; (+)-trans, 41.5%; and (−)-trans, 46.7%.

EXAMPLE 12

In a 50 ml flask were charged 1.0 g of the same (−)-rich chrysanthemic acid chloride as used in Example 4, 5 ml of toluene and 0.17 g of benzoyl peroxide under nitrogen and thereto was added dropwise 1 ml of a solution of N-bromosuccinimide (0.095 g) in acetone with stirring at 80° C.

After stirring at the same temperature for 30 minutes, a portion of the reaction mixture was sampled and converted into d-2-octyl ester by a conventional method. Gas chromatography assay of the chrysanthemic acid gave the following optical isomer ratio: (+)-cis, 5.5%; (−)-cis, 5.7%; (+)-trans, 41.6%; and (−)-trans, 47.2%.

EXAMPLE 13

In a 100 ml flask were charged 5.0 g of (−)-rich chrysanthemic acid chloride (composition: (+)-cis, 0.7%; (−)-cis, 17.5%; (+)-trans, 3.7%; and (−)-trans, 78.1%), 43.6 g of toluene and 43.5 mg of t-butyl hydroperoxide and thereto was added dropwise 0.4 ml of a solution of phosphorus tribromide (0.11 g) in toluene from a dropping funnel at 20°–25° C. over a period of 5 minutes, followed by stirring at the same temperature for 30 minutes. After the reaction, a portion of the reaction mixture was sampled and amount of chrysanthemic acid chloride was measured by gas chromatography to obtain 4.91 g. The sampled reaction mixture was converted into d-2-octyl ester by a conventional method. Gas chromatography assay gave the following optical isomer ratio: (+)-cis, 3.8%; (−)-cis, 3.8%; (+)-trans, 45.7%; and (−)-trans, 46.7%.

EXAMPLE 14

In a 100 ml flask were charged 5.0 g of (−)-cis chrysanthemic acid chloride and 40 g of toluene under nitrogen and thereto was added in parallel 1 ml of a solution of phosphorus tribromide (94.3 mg) in toluene and 1 ml of a solution of t-butyl hydroperoxide (36.2 mg) in toluene with stirring at 20°–25° C. over a period of 10 minutes. After stirring at the same temperature for 20 minutes, a portion of the reaction mixture was sampled and amount of chrysanthemic acid chloride was measured to obtain 4.92 g.

The sampled reaction mixture was converted into d-2-octyl ester by a conventional method. Gas chromatography assay gave the following optical isomer ratio: (+)-cis, 3.7%; (−)-cis, 4.0%; (+)-trans, 46.1%; and (−)-trans, 46.2%.

EXAMPLE 15

In a 100 ml flask were charged 2.5 g of the same (−)-rich chrysanthemic acid chloride as used in Example 13, 25.6 g of dioxane and 60.4 mg of t-butyl hydroperoxide under nitrogen and thereto was added 0.29 g of phosphorus pentabromide with stirring at 20°–25° C.

After stirring at the same temperature for 30 minutes, a portion of the reaction mixture was sampled and converted into d-2-octyl ester by a conventional method. Gas chromatography assay of the chrysanthemic acid gave the following optical isomer ratio: (+)-cis, 4.4%; (−)-cis, 4.4%; (+)-trans, 45.0%; and (−)-trans, 46.2%.

EXAMPLE 16

In a 50 ml flask were charged 2.5 g of the same (−)-rich chrysanthemic acid chloride as used in Example 13, 25.6 g of dioxane and 60 mg of t-butyl hydroperoxide under nitrogen and thereto was added dropwise 1 ml of a solution of trimethylsilyl bromide (200 mg) in dioxane with stirring at 20°–25° C.

After stirring at the same temperature for 30 minutes, a portion of the reaction mixture was sampled and converted into d-2-octyl ester by a conventional method. Gas chromatography assay of the chrysanthemic acid gave the following optical isomer ratio: (+)-cis, 4.6%; (−)-cis, 4.6%; (+)-trans, 43.5%; and (−)-trans, 47.3%.

EXAMPLE 17

In a 100 ml flask were charged 2.5 g of the same (−)-rich chrysanthemic acid chloride as used in Example 13, 33.2 g of dioxane and 8.4 mg of 60% aqueous hydrogen peroxide under nitrogen and thereto was added dropwise 0.36 g of phosphorus tribromide with stirring at 20°–25° C.

After stirring at the same temperature for 15 minutes, a portion of the reaction mixture was sampled and converted into d-2-octyl ester by a conventional method. Gas chromatography assay of the chrysanthemic acid gave the following optical isomer ratio: (+)-cis, 4.4%; (−)-cis, 4.5%; (+)-trans, 45.2%; and (−)-trans, 45.9%.

EXAMPLE 18

In a 100 ml flask were charged 2.5 g of the same (−)-rich chrysanthemic acid chloride as used in Example 13, 21.8 g of toluene and 0.13 g of t-butyl perbenzoate under nitrogen and thereto was added dropwise 0.66 ml of a solution of phosphorus tribromide (0.18 g) in benzene with stirring at 70°–75° C.

After stirring at the same temperature for 30 minutes, a portion of the reaction mixture was sampled and converted into d-2-octyl ester by a conventional method. Gas chromatography assay of the chrysanthemic acid gave the following optical isomer ratio: (+)-cis, 4.6%; (−)-cis, 6.3%; (+)-trans, 37.1%; and (−)-trans, 52.0%.

EXAMPLE 19

In a 100 ml flask were charged 2.5 g of the same (−)-rich chrysanthemic acid chloride as used in Example 13, 21.8 g of benzene and 0.11 g of azobisisobutyronitrile under nitrogen and thereto was added dropwise 0.67 ml of a solution of phosphorus tribromide (0.18 g) in benzene with stirring at 70°–75° C.

After stirring at the same temperature for 30 minutes, a portion of the reaction mixture was sampled and converted into d-2-octyl ester by a conventional method. Gas chromatography assay of the chrysanthemic acid gave the following optical isomer ratio: (+)-cis, 4.8%; (−)-cis, 5.0%; (+)-trans, 44.5%; and (−)-trans, 45.7%.

Content of chrysanthemic acid chloride in the reaction mixture was measured by gas chromatography to obtain 2.45 g.

EXAMPLE 20

In a 100 ml flask were charged 2.5 g of the same (−)-rich chrysanthemic acid chloride as used in Example 13, 25 ml of toluene and 60 mg of t-butyl hydroperoxide under nitrogen and thereto was added dropwise 1.3 ml of a solution of silicon tetrabromide (0.23 g) in toluene at 20°–25° C.

After stirring at the same temperature for 30 minutes, a portion of the reaction mixture was sampled and converted into d-2-octyl ester by a conventional method. Gas chromatography assay of the chrysanthemic acid gave the following optical isomer ratio: (+)-cis, 4.2%; (−)-cis, 4.5%; (+)-trans, 43.6%; and (−)-trans, 47.7%.

EXAMPLE 21

1.24 Grams of chrysanthemic acid chloride (composition: (+)-cis, 1.8%; (−)-cis, 18.3%; (+)-trans, 11.1%; and (−)-trans; 68.8%) and 82 mg of azobisisobutyronitrile were dissolved in 5.0 ml of toluene and to the solution was added dropwise a solution of thiophenol (100 mg) in toluene with stirring at 80° C., followed by stirring at the same temperature for 30 minutes. Gas chromatography assay of the reaction mixture gave the following optical isomer ratio: (+)cis, 5.6%; (−)-cis, 5.8%; (+)-trans, 42.5%; and (−)trans, 46.1%.

EXAMPLE 22

In a 100 ml flask were charged 2.0 g of (−)-rich chrysanthemic acid chloride as used in Example 21, 8.0 g of toluene and 0.21 g of t-butyl perbenzoate under nitrogen and thereto was added dropwise a solution of thiobenzoic acid (0.22 g) in toluene with stirring at 100° C., followed by stirring at the same temperature for 30 minutes.

Gas chromatography assay gave the following optical isomer ratio: (+)-cis, 6.8%; (−)-cis, 6.9%; (+)-trans, 41.6%; and (−)-trans, 44.7%.

EXAMPLE 23

In a 50 ml flask were charged 2.0 g of (−)-rich chrysanthemic acid anhydride (composition: (+)-cis, 0.7%; (−)-cis, 17.5%; (+)-trans, 3.7%; and (−)trans, 78.1%) and 20.0 g of toluene under nitrogen and then thereto were added in parallel 1 ml of a solution of t-butyl hydroperoxide (0.17 g) in toluene and 1 ml of a solution of phosphorus tribromide (0.51 g) in toluene over a period of 10 minutes at 80° C. with stirring.

After stirring at same temperature for 30 minutes, a portion of the reaction mixture was sampled and converted into d-2-octyl ester. Gas chromatography assay of the chrysanthemic acid gave the following optical isomer ratio: (+)-cis, 3.7%; (−)-cis, 3.7%; (+)-trans, 46.0%; and (−)-trans, 46.6%.

EXAMPLE 24

In a 50 ml flask were charged 2.0 g of (−)-rich chrysanthemic acid anhydride as used in Example 23, 20.0 g of benzene and azobisisobutyronitrile (0.16 g) under nitrogen and then thereto was added N-bromosuccinimide (0.22 g) with stirring at 80° C.

After stirring at same temperature for 30 minutes, a portion of the reaction mixture was sampled and converted into d-2-octyl ester. Gas chromatography assay of the chrysanthemic acid gave the following optical isomer ratio: (+)-cis, 3.7%; (−)-cis, 3.9%; (+)-trans, 43.6%; and (−)-trans, 48.6%.

EXAMPLE 25

In a 100 ml flask were charged 5.0 g of chrysanthemic acid chloride comprising cis-isomer 35% and trans-isomer 65%, 43.6 g of toluene and 43.5 mg of t-butyl hydroperoxide under nitrogen and then thereto was added dropwise 1 ml of a solution of hydrogen bromide (0.11 g) in dioxane at 20°–25° C. over a period of 5 minutes.

After stirring at the same temperature for 30 minutes, a portion of the reaction mixture was sampled and converted into an ethyl ester by a conventional method. Gas chromatography assay of the chrysanthemic acid gave the isomer ratio of cis-isomer: 7.8% and trans-isomer: 92.2%.

Content of chrysanthemic acid chloride was 4.91 g measured by gas chromatography.

EXAMPLE 26

In a 100 ml flask were charged 5.0 g of cis-chrysanthemic acid chloride and 40 g of toluene under nitrogen and thereto were added in parallel 1 ml of a solution of hydrogen bromide (87 mg) in dioxane and 1 ml of a solution of t-butyl hydroperoxide (43.5 mg) in toluene with stirring at 20°–25° C. over a period of 10 minutes, followed by stirring at the same temperature for 20 minutes. A portion of the reaction mixture was sampled and converted into an ethyl ester. Gas chromatography assay gave the isomer ratio of cis-isomer: 8.0% and trans-isomer: 92.0%. Content of chrysanthemic acid chloride in the reaction mixture was 4.92 g.

EXAMPLE 27

In a 100 ml flask were charged 2.5 g of the same crysanthemic acid chloride as used in Example 25, 24.1 g of dioxane and 200 mg of cumene hydroperoxide and thereto was added dropwise 0.25 g of acetyl bromide at 20°–25° C.

After stirring at the same temperature for 30 minutes, a portion of the reaction mixture was sampled and converted into an ethyl ester. Gas chromatography assay of the chrysanthemic acid chloride gave the isomer ratio of cis-isomer: 8.0% and transisomer: 92.0%.

EXAMPLE 28

In a 100 ml flask were charged 2.5 g of the same chrysanthemic acid chloride as used in Example 25, 24.0 g of dioxane and 120 mg of t-butyl hydroperoxide under nitrogen and thereto was added dropwise 0.42 g of thionyl bromide at 20°–25° C.

After stirring at the same temperature for 30 minutes, a portion of the reaction mixture was sampled and converted into an ethyl ester. Gas chromatography assay of the chrysanthemic acid chloride gave the isomer ratio of cis-isomer: 8.3% and transisomer: 91.7%.

EXAMPLE 29

In a 100 ml flask were charged 2.5 g of the same chrysanthemic acid chloride as used in Example 25, 10.4 g of toluene and 154 mg of methyl azobisisobutyrate under nitrogen and thereto was added dropwise 0.21 g of bromine at 70°–75° C.

After stirring at the same temperature for 30 minutes, a portion of the reaction mixture was sampled and converted into an ethyl ester. Gas chromatography assay of the chrysanthemic acid chloride gave the isomer ratio of cis-isomer: 9.9% and transisomer: 90.1%.

EXAMPLE 30

In a 100 ml flask were charged 2.5 g of chrysanthemic acid chloride comprising cis-isomer 35% and trans-isomer 65%, 25.6 g of chlorobenzene and 60 mg of t-butyl hydroperoxide under nitrogen and thereto was added dropwise 0.31 g of chrysanthemic acid bromide comprising cis-isomer 8.4% and trans-isomer 91.6% at 20°–25° C.

After stirring at the same temperature for 30 minutes, a portion of the reaction mixture was sampled and converted into an ethyl ester. Gas chromatography assay of the chrysanthemic acid chloride gave the isomer ratio of cis-isomer: 8.5% and transisomer: 91.5%.

EXAMPLE 31

In a 100 ml flask were charged 1.0 g of the same chrysanthemic acid chloride as used in Example 25, 4.4 g of toluene and 88 mg of azobisisobutyronitrile under nitrogen and then thereto was added dropwise 1 ml of a solution of N-bromosuccinimide (0.095 g) in acetone at 75°–80° C.

After stirring at the same temperature for 30 minutes, a portion of the reaction mixture was sampled and converted into an ethyl ester. Gas chromatography assay of the chrysanthemic acid chloride gave the isomer ratio of cis-isomer: 11.8% and transisomer: 88.2%.

EXAMPLE 32

In a 100 ml flask were charged 2.5 g of the same chrysanthemic acid chloride as used in Example 25, 30 g of dioxane and 8.4 mg of 60% aqueous hydrogen peroxide under nitrogen and thereto were added dropwise 3 ml of a solution of hydrogen bromide (0.32 g) in dioxane at 20°–25° C.

After stirring at the same temperature for 30 minutes, a portion of the reaction mixture was sampled and converted into an ethyl ester. Gas chromatography assay of the chrysanthemic acid chloride gave the isomer ratio of cis-isomer: 8.7% and transisomer: 91.3%.

EXAMPLE 33

In a 100 ml flask were charged 2.5 g of the same chrysanthemic acid chloride as used in Example 25, 21.8 g of toluene and 140 mg of t-butyl perbenzoate and thereto was added dropwise 1.6 ml of a solution of hydrogen bromide (0.16 g) in dioxane at 75°–80° C.

After stirring at the same temperature for 30 minutes, a portion of the reaction mixture was sampled and converted into an ethyl ester. Gas chromatography assay of the chrysanthemic acid chloride gave the isomer ratio of cis-isomer: 11.3% and transisomer: 88.7%.

EXAMPLE 34

In a 100 ml flask were charged 5.0 g of cis-chrysanthemic acid chloride and 40 g of toluene under nitrogen and thereto were added in parallel 1 ml of a solution of phosphorus tribromide (94.3 mg) in toluene and 1 ml of a solution of t-butyl hydroperoxide (36.2 mg) in toluene with stirring at 20°–25° C. over a period of 10 minutes. After stirring at the same temperature for 20 minutes, a portion of the reaction mixture was sampled and converted into an ethyl ester by a conventional method. Gas chromatography assay gave the isomer ratio of cis-isomer: 7.7% and trans-isomer: 92.3%. Content of chrysanthemic acid chloride was 4.92 g.

EXAMPLE 35

In a 100 ml flask were charged 5.0 g of chrysanthemic acid chloride comprising cis-isomer 35% and trans-isomer 65%, 43.6 g of toluene and 43.5 mg of t-butyl hydroperoxide under nitrogen and thereto was added dropwise 0.4 ml of a solution of phosphorus tribromide (0.11 g) in toluene from a dropping funnel at 20°–25° C. over a period of 5 minutes, followed by stirring at the same temperature for 30 minutes. After the reaction, a portion of the reaction mixture was sampled and converted into an ethyl ester by a conventional method. Gas chromatography assay gave the isomer ratio of cis-isomer: 7.6% and trans-isomer: 92.4%. Content of chrysanthemic acid chloride was 4.91 g.

EXAMPLE 36

In a 100 ml flask were charged 2.5 g of chrysanthemic acid chloride comprising cis-isomer 35% and trans-isomer 65%, 24.6 g of dioxane and 60.4 mg of t-butyl hydroperoxide under nitrogen and thereto was added dropwise 1 ml of a solution of phosphorus pentabromide (0.29 g) in dioxane at 20°–25° C.

After stirring at the same temperature for 30 minutes, a portion of the reaction mixture was sampled and converted into an ethyl ester. Gas chromatography assay of the chrysanthemic acid chloride gave the isomer ratio of cis-isomer: 8.8% and trans-isomer 91.2%.

EXAMPLE 37

In a 100 ml flask were charged 2.5 g of the same chrysanthemic acid chloride as used in Example 36, 33.2 g of dioxane and 8.4 mg of 60% aqueous hydrogen peroxide under nitrogen and then thereto was added dropwise 0.36 g of phosphorus tribromide at 20°–25° C.

After stirring at the same temperature for 30 minutes, a portion of the reaction mixture was sampled and converted into an ethyl ester. Gas chromatography assay of the chrysanthemic acid chloride gave the isomer ratio of cis-isomer: 8.9% and transisomer: 91.1%.

EXAMPLE 38

In a 100 ml flask were charged 2.5 g of cis-chrysanthemic acid chloride, 24.6 g of dioxane and 60 mg of t-butyl hydroperoxide under nitrogen and thereto were added dropwise 1 ml of a solution of trimethylsilyl bromide (0.2 g) in dioxane at 20°–25° C.

After stirring at the same temperature for 30 minutes, a portion of the reaction mixture was sampled and converted into an ethyl ester. Gas chromatography assay of the chrysanthemic acid chloride gave the isomer ratio of cis-isomer: 9.1% and transisomer: 90.9%.

EXAMPLE 39

In a 100 ml flask were charged 2.5 g of the same chrysanthemic acid chloride as used in Example 36, 21.0 g of toluene and 130 mg of t-butyl perbenzoate and thereto was added dropwise 1 ml of a solution of phosphorus tribromide (0.18 g) in toluene at 70°–75° C.

After stirring at the same temperature for 30 minutes, a portion of the reaction mixture was sampled and converted into an ethyl ester. Gas chromatography assay of the chrysanthemic acid chloride gave the isomer ratio of cis-isomer: 10.9% and trans-isomer: 89.1%.

EXAMPLE 40

In a 100 ml flask were charged 2.5 g of the same chrysanthemic acid chloride as used in Example 36, 21.8 g of benzene and 110 mg of azobisisobutyronitrile under nitrogen and thereto was added dropwise 0.18 g of phosphorus tribromide at 70°–75° C.

After stirring at the same temperature for 30 minutes, a portion of the reaction mixture was sampled and converted into an ethyl ester. Gas chromatography assay of the chrysanthemic acid chloride gave the isomer ratio of cis-isomer: 9.8% and trans-isomer: 90.2%.

EXAMPLE 41

In a 100 ml flask were charged 2.5 g of the same chrysanthemic acid chloride as used in Example 36, 21.8 g of toluene and 100 mg of cumene hydroperoxide under nitrogen and thereto was added dropwise 0.23 g of silicon tetrabromide at 20°–25° C.

After stirring at the same temperature for 30 minutes, a portion of the reaction mixture was sampled and converted into an ethyl ester. Gas chromatography assay of the chrysanthemic acid chloride gave the isomer ratio of cis-isomer: 8.7% and transisomer: 91.3%.

EXAMPLE 42

In a 100 ml flask were charged 2.0 g of chrysanthemic acid chloride comprising cis-isomer 35% and trans-isomer 65%, 10 g of benzene and 0.43 g of lauroyl peroxide under nitrogen and thereto was added dropwise a solution of thiosalicylic acid (0.25 g) in dioxane at 70° C.

After stirring at the same temperature for 30 minutes, a portion of the reaction mixture was sampled and converted into an ethyl ester. Gas chromatography assay gave the isomer ratio of cisisomer: 6.9% and trans-isomer 93.1%.

EXAMPLE 43

In a 50 ml flask were charged 2.0 g of cis chrysanthemic acid anhydride and 20 g of toluene under nitrogen and then thereto were added in parallel 1 ml of a solution of azobisisobutyronitrile (0.30 g) in toluene and 1 ml of a solution of p-thiocresol (0.23 g) in toluene over a period of 10 minutes at 80° C. with stirring.

After stirring at same temperature for 4 hours, a portion of the reaction mixture was sampled and converted into carboxylic acid. Gas chromatography assay of the chrysanthemic acid gave the isomer ratio of cis-isomer: 6.8% and trans-isomer: 93.2%.

We claim:

1. A method for preparing racemized chrysanthemic acid derivatives by treating an optically active chrysanthemic acid derivatives having the formula:

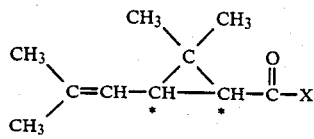

wherein X represents a chlorine atom, a bromine atom or 2,2-dimethyl-3-isobutenyl-cyclopropane carboxyl group and * mark represents asymmetric carbon atom, which comprises contacting with at least one compound selected from the group consisting of hydrogen bromide, a carboxylic acid bromide, an N-bromine compound, an S-bromine compound, a halo-bromine compound, a silicon-bromide compound, a phosphorus-bromide compound and an SH compound in the presence of a peroxide or an azo compound.

2. A method according to claim 1 wherein the peroxide is at least one compound selected from the group consisting of hydroperoxides, diacyl peroxides, peroxy esters, ketone peroxides, dialkyl peroxides, peracids and hydrogen peroxide.

3. A method according to claim 1 or 2 wherein the peroxide is hydroperoxides, diacyl peroxides, hydrogen peroxide or peroxy esters.

4. A method according to claim 1 wherein the azo compound is at least one compound selected from the group consisting of azonitriles, azo esters and alkylazo compounds.

5. A method according to claim 1 or 4 wherein the azo compound is at least one compound selected from the group consisting of azonitriles and azo esters.

6. A method according to claim 1, 2, 3, 4 or 5 wherein the carboxylic acid bromides have 1–18 carbon atoms.

7. A method according to claim 1, 2, 3, 4 or 5 wherein the N-bromine compound is selected from the group consisting of N-bromoimide and N-bromoamide.

8. A method according to claim 1, 2, 3, 4 or 5 wherein the S bromine compound is selected from the group consisting of thionyl bromide, sulfuryl bromide, arylsulfonyl bromide, arylsulfinyl bromide, lower alkylsulfonyl bromide, and alkyl sulfinyl bromide.

9. A method according to claim 1, 2, 3, 4 or 5 wherein the halo-bromine compound is selected from the group consisting of bromine, iodine bromide and iodine tribromide.

10. A method according to claim 1, 2, 3, 4 or 5 wherein the silicon bromide is selected from the group consisting of lower alkylsilyl bromide, arylsilyl bromide and silyl tetrabromide.

11. A method according to claim 1, 2, 3, 4 or 5 wherein the phosphorus-bromide compound is at least one compound selected from the group consisting of phosphorus tribromide, phosphorus pentabromide, phosphorus oxybromide, and organic phosphorus bromide.

12. A method according to claim 1, 2, 3, 4 or 5 wherein the SH compound is selected from the group consisting of thiol, thiocarboxylic acid and dithio acid.

13. A method for conversion of cis isomer or of a mixture of cis and trans isomers of chrysanthemic acid derivatives having the formula:

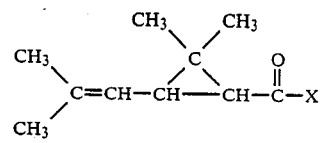

wherein X represents a chlorine atom, a bromine atom or 2,2-dimethyl-3-isobutenyl-cyclopropane carboxyl group, to the corresponding trans-rich chrysanthemic acid derivatives, which comprises contacting the acid derivatives described above with at least one compound selected from the group consisting of hydrogen bromide, a carboxylic acid bromide, an N-bromine compound, an S-bromine compound, a halo-bromine compound, a silicon-bromide, a phosphorus-bromide compound and an SH compound in the presence of a peroxide or an azo compound.

14. A method according to claim 13 wherein the peroxide is at least one compound selected from the group consisting of hydroperoxides, diacyl peroxides, peroxy esters, ketone peroxides, dialkyl peroxides, peracids and hydrogen peroxide.

15. A method according to claim 13 or 14 wherein the peroxide is hydroperoxides, diacyl peroxides, hydrogen peroxide or peroxy esters.

16. A method according to claim 13 wherein the azo compound is at least one compound selected from the group consisting of azonitriles, azo esters and alkylazo compounds.

17. A method according to claim 13 or 14 wherein the azo compound is at least one compound selected from the group consisting of azonitriles and azo esters.

18. A method according to claim 13, 14, 15, 16 or 17 wherein the carboxylic acid bromides have 1–18 carbon atoms.

19. A method according to claim 13, 14, 15, 16 or 17 wherein the N-bromine compound is selected from the group consisting of N-bromoimide and N-bromoamide.

20. A method according to claim 13, 14, 15, 16 or 17 wherein the S-bromine compound is selected from the group consisting of thionyl bromide, sulfuryl bromide, arylsulfonyl bromide, arylsulfinyl bromide, lower alkylsulfonyl bromide, and alkyl sulfinyl bromide.

21. A method according to claim 13, 14, 15, 16 or 17 wherein the halo-bromine compound is selected from the group consisting of bromine, iodine bromide and iodine tribromide.

22. A method according to claim 13, 14, 15, 16 or 17 wherein the silicon bromide is selected from the group consisting of lower alkylsilyl bromide, arylsilyl bromide and silyl tetrabromide.

23. A method according to claim 13, 14, 15, 16 or 17 wherein the SH compound is selected from the group consisting of thiol, thiocarboxylic acid and dithio acid.

24. A method according to claim 13, 14, 15, 16 or 17 wherein the phosphorus bromide compound is at least one compound selected from the group consisting of phosphorus tribromide, phosphorus pentabromide, phosphorus oxybromide, and organic phosphorus bromide.

* * * * *